Figure 1:
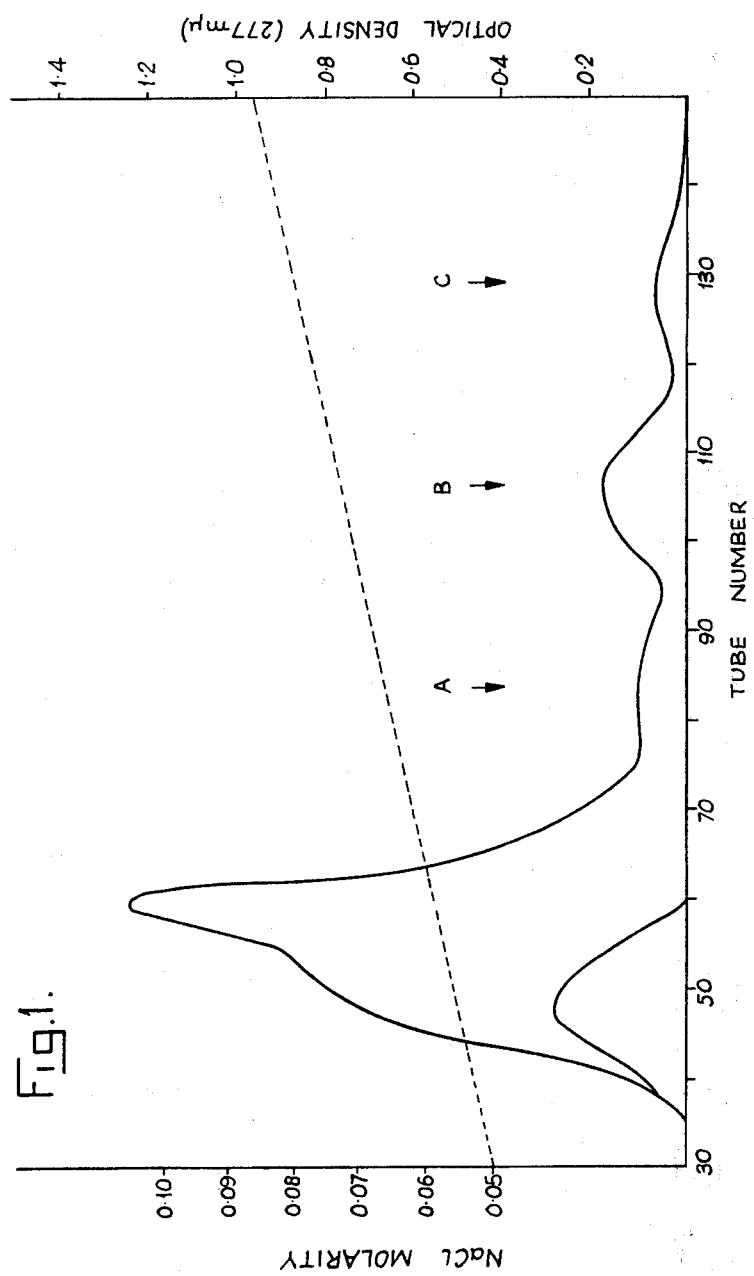

United States Patent [19]

Lindsay et al.

[11] 3,950,517

[45] Apr. 13, 1976

[54] INSULIN DERIVATIVES

[75] Inventors: David Gordon Lindsay, Hove; Sydney Shall, Lewes, both of England

[73] Assignee: National Research Development Corporation, London, England

[22] Filed: Dec. 6, 1974

[21] Appl. No.: 530,143

Related U.S. Application Data

[60] Division of Ser. No. 390,216, Aug. 21, 1973, Pat. No. 3,869,437, which is a continuation-in-part of Ser. No. 89,816, Nov. 16, 1970, abandoned.

[30] Foreign Application Priority Data

May 8, 1970 United Kingdom............... 22342/70

[52] U.S. Cl. ............................................... 424/178
[51] Int. Cl.² ........................................ A61K 37/26
[58] Field of Search .................................... 424/178

[56] References Cited
UNITED STATES PATENTS
3,823,125  7/1974  Grant et al........................... 424/178

Primary Examiner—Frederick E. Waddell

[57] ABSTRACT

A physiologically acceptable insulin derivative has the terminal amino group of the B chain ($B_1$, phenylalanine) protected by an acyl group or other blocking group containing up to 7 carbon atoms and the amino group of the A chain ($A_1$, glycine) is either free or protected by means of an acyl or other blocking group containing no more than four carbon atoms and preferably no more than three atoms other than hydrogen. Pharmaceutical preparations may be prepared containing an effective amount of such an insulin derivative together with a physiologically acceptable diluent. An insulin derivative of reduced antigenicity is obtainable from porcine or bovine insulin by reacting the insulin with an acylating agent or other blocking reagent to acylate or otherwise block the amino group of the $B_1$ amino acid and optionally block the $A_1$ and/or $B_{29}$ amino acid, followed by purification of the derivative by various methods.

29 Claims, 7 Drawing Figs.

INSULIN DERIVATIVES

This is a division of application Ser. No. 390,216 filed Aug. 21, 1973 now U.S. Pat. No. 3,869,437, which itself is a continuation-in-part of Ser. No. 89,816 filed Nov. 16, 1970, now abandoned.

This invention relates to insulin derivatives.

Porcine and bovine insulin have been used clinically for many years in the treatment of diabetes and other disorders. One of the disadvantages of these materials however is that for certain patients it is necessary after treatment has been continued for some time to increase the dose in order to produce the required effect. This has been explained by ascribing antigenic properties to those non-human insulins which give rise to antibodies in sufficient amount to counteract a proportion of the dose of insulin applied.

It has now been found possible to reduce considerably and perhaps even eliminate the ability of porcine and bovine insulins to react with specific insulin antibody without unduly affecting the desirable properties of these hormones.

In accordance with this invention physiologically acceptable substantially pure mono-, di- or tri-substituted insulin derivatives having reduced reactivity to insulin antibodies are those in which the terminal amino group of the B chain ($B_1$ phenylalanine) is protected by an acyl group or other blocking group containing up to 7 carbon atoms and the amino group of the A chain ($A_1$, glycine) is either free or protected by means of an acyl or other blocking group containing no more than four carbon atoms and no free primary amino group. The blocking groups in each case may be straight or branched chain or cyclic radicals containing carbon and if desired other elements including, for example, oxygen, nitrogen and sulphur. The term "pure" is used in this specification to mean free from by-products of manufacture. It therefore embraces not only monocomponent preparations in which the customary pharmaceutical additives are present but multicomponent preparations based on individually pure and defined components. Another very valuable type of blocking group on the $A_1$ glycine amino group is one which contains no more than three atoms other than hydrogen.

Although insulin has been subjected to many substitution reactions in the past the results recorded in the literature are complex and difficult to interpret due chiefly to the fact that such reactions give rise to a complex mixture of products and unless proper care is taken in the separation and purification of various products, it is impossible to reach firm conclusions as to the biological properties of the derivatives so formed. Most workers have reported a substantial loss in activity and it has not been recognised, prior to the present invention, that by careful selection of the substituent protective groups derivatives may be produced which have blood sugar lowering properties very similar to that of the parent insulin, at least as regards the initial effect upon intravenous injection into experimental animals, but have significantly reduced reactivity towards specific insulin antibodies. To achieve these effects the nature and size of the protective group on the B chain in the compounds of the present invention is not as critical as that on the A chain and it will be appreciated that different blocking groups may be used for the respective amino groups. However in practice it is considerably more convenient to use the same blocking group for both amino groups, and also for the third amino group of the $B_{29}$ amino acid (lysine) where tri-substituted derivatives are formed.

Protection of the desired amino groups is readily achieved by acylation. Subject to the qualifications expressed above with regard to the protective groups, a wide variety of acylating agents may be used to introduce groups such as formyl, acetyl, trifluoroacetyl, hydroxypropionyl, cyclopropane-carbonyl, acetoacetyl and other aliphatic acyl groups, benzoyl and other aroyl groups as well as those derived from heterocyclic compounds e.g. 2,2-dimethyl-3-formyl-L-thiazolidine-4-carboxylic esters. Acylation may be conducted by any of the standard methods employed in peptide chemistry including especially the use of activated esters or anhydrides and typical carbodiimide coupling reagents. Acylating agents which are esters of N-hydroxysuccinimide are particularly advantageous. A variety of alternative blocking groups include those which introduce the carbamyl, thiocarbamyl, alkyl carbamyl and alkyl thiocarbamyl groups, amidino groups,

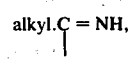

and the guanidino group,

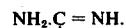

The amidino group

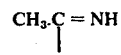

for example, is introduced by means of ethyl acetimidate hydrochloride and the guanidino group by means of O-methyl isourea. Other blocking groups are, for example $HOCH_2CH_2CO-$ (introduced by butyrolactone) $HOOC.CH_2CO-$ and the corresponding group $H_2NOC.CH_2CO-$ (introduced by the corresponding activated ester of malonic acid or malonamide). The use of more complex acylating and other groups may introduce more difficult separation problems and it is believed that simple acetylation will in practice be most attractive and conducting the reaction to produce the greatest yield of the triacetyl ($A_1$, $B_1$, $B_{29}$ substituted), derivative is a particularly recommended procedure in accordance with this invention.

In order to produce the maximum yield of insulin acylated at the $B_1$ amino group the proportion of acylating agent or other blocking reagent used is preferably relatively low. For example, reacting one mole of the insulin with from about one to not more than about two moles of acylating agent produces the $B_1$ mono-substituted derivative in the largest amounts. Mono-substitution at other amino groups can however also occur leading to by-products which are less useful. Furthermore, after substitution at $B_1$ a certain degree of di-substitution and even tri-substitution can take place especially when three to four moles of acylating or other reagent are used. It has also been found that the acylation reaction depends on the pH of the reaction medium. To produce the best yield of mono-substitution product at the $B_1$ amino group, the pH is preferably at or near about 7.0 and preferably no greater than about 8. At pH 8.5 to 9 for example the yield of this desired product falls off considerably in favour of additional substitution at $A_1$ and $B_{29}$. Usually it will be desirable to isolate the required derivative by means of chromatography, electrophoresis, or any other conventional method of purifying peptides amenable to use on a large scale.

The insulin derivatives of the present invention exhibit of the order of at least 75% and preferably at least 90% of the normal insulin type of blood sugar lowering activity, weight for weight, as tested by intravenous injection into laboratory animals and measurement of the effect within a 30 minute period after injection. In most cases the new derivatives have an initial bloor sugar lowering effect which is virtually indistinguishable from insulin itself. In contrast the derivatives have less than about 50% of the immunoreactivity of the parent insulin as determined by radioimmunoassay. In many cases the reduction in immunoreactivity (reactivity towards specific insulin antibody) is as low as 30% or even 10% of that of the parent hormone. Comparative figures are shown in the following Tables. The figures are expressed on a percentage basis relative to insulin.

form e.g. by freeze-drying following which it may be made up to the required concentration in an injectable physiologically acceptable diluent such as sterile pyrogen-free water or saline containing suitable buffers, and dispensed in ampoules.

Examples of typical derivatives produced in accordance with the invention will now be described.

EXAMPLE 1 a. N-Hydroxysuccinimide ester of 2,2-dimethyl-3-formyl-L-thiazolidine-4-carboxylic acid 3-Formyl-2,2-dimethyl-L-thiazolidine-4-carboxylic acid (9.46 g., 0.05 moles) was dissolved in redistilled dimethylformamide (50 ml.) and the solution cooled to 4°. Recrystallised N-hydroxy-succinimide (5.76 g., 0.05 moles) was added followed by N,N'-dicyclohexylcarbodiimide (10.32 g., 0.05 moles) and the solution stirred overnight at 4°, and for a further 2 hours at 25°. The dicyclohexylurea formed was filtered off and the dimethylformamide removed on a rotary evaporator under reduced pressure. The additional precipitate of dicyclohexylurea produced was filtered off and the urea was washed with dichloromethane. Petroleum ether (60°–80°) was added to the supernatant until the solution went turbid. Filtration of the crystalline mate-

TABLE 1

|  | Mouse convulsion assay Mean potency | Radioimmunoassay Immunoreactivity |
|---|---|---|
| Crystalline bovine insulin | 100 | 100 |
| $Phe^{B1}$-monosubstituted insulins |  |  |
| (a) Acetyl (bovine) | 100 | 30 |
| (b) Acetoacetyl (bovine) | 109 | 8.6 |
| (c) Thiazolidine (bovine) | 103 | 27 |
| $Gly^{A1}$-monosubstituted insulins |  |  |
| (a) Acetyl (bovine) | 105 | 71 |
| (b) Acetoacetyl (bovine) | 88 | 87 |
| (c) Thiazolidine (bovine) | 57 | 81 |
| $Lys^{B29}$-monosubstituted insulins |  |  |
| (a) Acetyl (bovine) | 114 | 83 |
| (b) Thiazolidine (bovine) | 101 | 84 |
| $Phe^{B1}$, $Gly^{A1}$-disubstituted insulins |  |  |
| (a) Acetyl (porcine) | 90 | 25 |
| (b) Acetoacetyl (bovine) | 76 | 14 |
| $Gly^{A1}$, $Lys^{B29}$-disubstituted insulin |  |  |
| (a) Acetyl (porcine) | 93 | 67 |
| $Phe^{B1}$, $Gly^{A1}$, $Lys^{B29}$-trisubstituted insulins |  |  |
| (a) Acetyl (porcine) | 96 | 10 |
| (b) Acetoacetyl (bovine) | 77 | 17 |

TABLE 2

|  | Blood sugar lowering | Immunoreactivity |
|---|---|---|
| Crystalline bovine insulin | 100 | 100 |
| $Phe^{B1}$-monosubstituted insulin |  |  |
| (a) carbamyl | 100 | 23 |
| (b) methylthiocarbamyl | 100 | 28 |
| $Gly^{A1}$-monosubstituted insulin |  |  |
| (a) carbamyl | 100 |  |
| (b) methylthiocarbamyl | 100 | 92 |
| $Phe^{B1}$-$Gly^{A1}$-disubstituted insulins |  |  |
| (a) carbamyl | 100 | 10 |
| (b) methylthiocarbamyl | 100 | 20 |
| $Phe^{B1}$-$Gly^{A1}$-$Lys^{B29}$tricarbamyl insulin | 100 | 9 |

Insulin derivatives in accordance with this invention may be formulated as pharmaceutical preparations in the same way as the parent insulins and may be used clinically at comparable and even lower dosage levels. Thus the desired derivative, after fractionation of the reaction mixture and removal of excess salts e.g. by dialysis, may be recovered in solution form or solid rial produced on standing after drying in a desiccator containing sodium hydroxide and paraffin wax, gave colourless needles of the N-hydroxysuccinimide derivative (13.7 g., 95.7%) m.p. 98°–100°.

b. Reaction of insulin with N-hydroxysuccinimide ester of 2,2-dimethyl-3-formyl-L-thioazolidine-4-carboxylic acid Zinc insulin (500 mg., 0.085 mM) (porcine) 10 times recrystallised (Novo Industri A/S, Copenhagen) was dissolved in hydrochloric acid (45 ml., 0.1N) and the pH adjusted with N sodium hydroxide to 6.9 in the titration vessel of a Radiometer (Type TTT1) pH-stat. The hydroxysuccinimide ester (22 mg., 0.085 mM) was dissolved in dioxane (100 $\mu$l) and added to the above solution in 10 $\mu$l aliquots, maintaining the pH at 6.9 by the addition of alkali, every 30 minutes.

After the final addition of the hydroxysuccinic ester the reaction mixture was made 0.2 M in sodium carbonate-sodium bicarbonate buffer pH 9.5 and left overnight. The material was lyophilised, after extensive dialysis against distilled water, to yield 490 mg. of the modified protein.

In a second experiment, zinc insulin (500 mg. 0.085 mM) was treated with hydroxysuccinic ester (32 mg., 0.127 mM) at pH 8.5 exactly as described above. The reaction rate as judged by the uptake of alkali was much faster than at pH 6.9 and aliquots were added every 5 minutes.

c. Separation of thiazolidine insulins i. Chromatography

The thiazolidine insulins were separated on a column of DEAE-Sephadex A-25 (2.5 × 40 cm.).

The column was equilibrated with buffer containing 0.01 M tris and 0.05 M sodium chloride in 7 M de-ionised urea at pH 7.29. Thiazolidine modified insulin was dissolved in this buffer (500 mg., 50 mg./ml.) and the column developed at a flow rate of 54.0 ml./hour collecting 12 ml. fractions. After 120 ml. of eluant was collected, a linear gradient, obtained by running 0.01 M tris, 0.01 sodium chloride in 7 M de-ionised urea (1 l.), at pH 7.29 into the stirred reservoir of the starting buffer, (1 l.) was applied.

The protein concentration was determined from the absorbance of the solution at 277 m$\mu$.

The appropriate fractions were pooled and extensively dialysed against distilled water. The material was lyophilised and the residue de-ionised on a column (1.5 × 60 cm.) of G.10 Sephadex equilibrated with 5% acetic acid. The protein fractions were collected and lyophilised.

Figure 2:
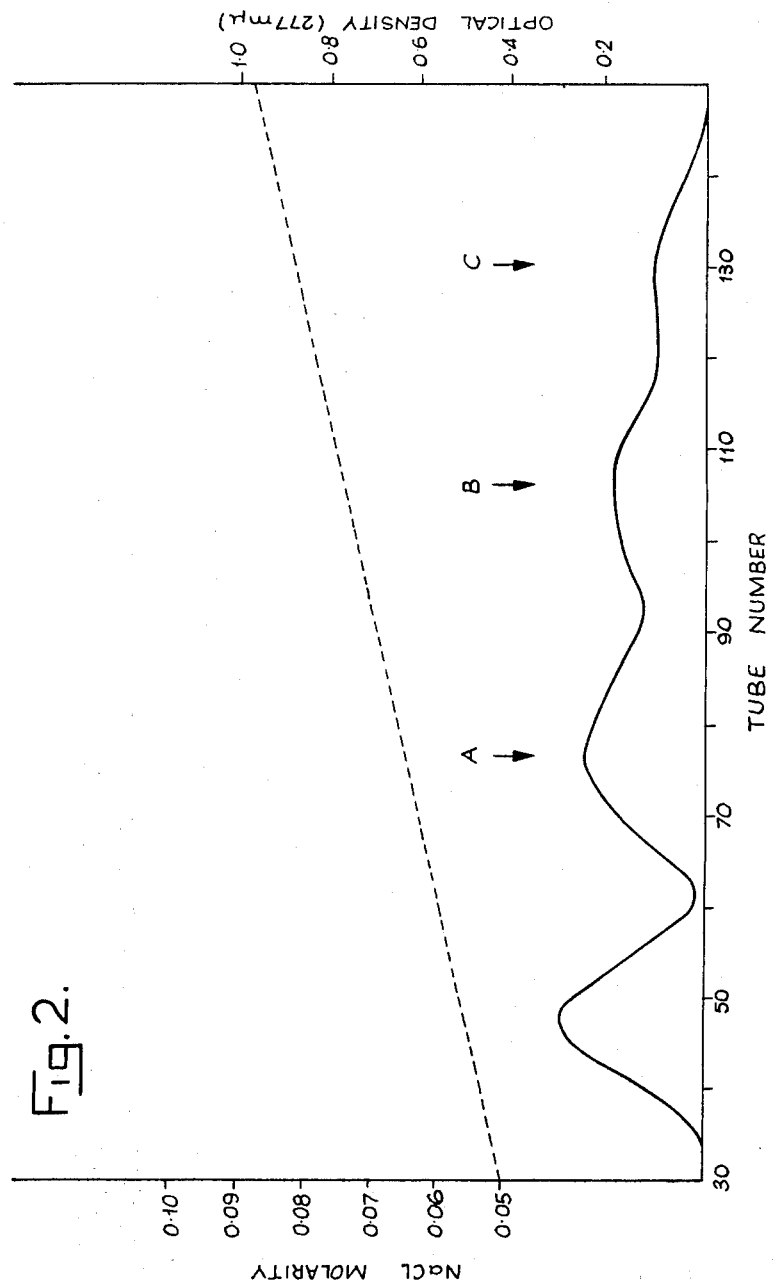

The chromatographic separation of the insulin derivatives formed from the above reaction can be seen in FIG. 1. Using a gentle salt gradient of 0.05 to 0.1 molar sodium chloride, incomplete separation of the peaks A, B and C occured. Material under peaks A, B and C was combined and re-chromatographed under exactly the same conditions to give the elution pattern shown in FIG. 2. Material about the centre of each peak was pooled and each individual peak subjected to re-chromatography to give three chromatographically homogenous fractions. The derivatives corresponding to peaks A, B and C were shown to be mono-substituted on phenylalanine, glycine and lysine respectively.

Figure 3:
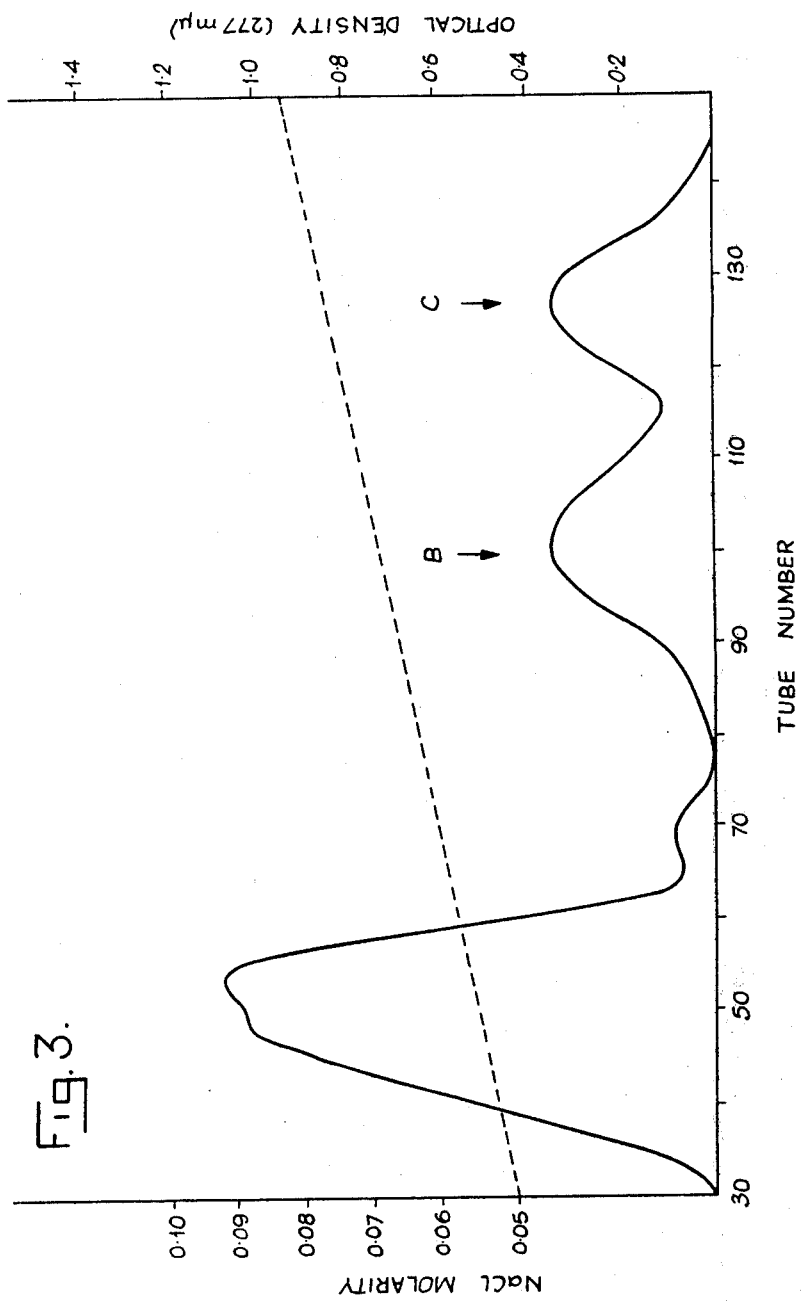

The elution pattern of the derivatives obtained when insulin was treated with a 1.5 molar excess of the acylating agent at pH 8.5 can be seen in FIG. 3. A much simpler elution pattern was obtained and material corresponding to derivative A in the previous chromatography was present in low amount.

ii. Cellulose acetate electrophoresis

For the separation of the thiazolidine insulins, the conditions were those described by Carpenter and Hayes (Biochemistry 2 (1963) 1272)) using a Shandon electrophoresis tank fitted with a water-cooled plate (20 × 20 cm.) and a power supply of 1 Kv. The buffer used was 0.065 M phosphate, 7 M urea, pH 6.5 and the cellulose acetate strips (20 × 5 cm.) were stained in a 0.2% solution of Ponceau S in 3% acetic acid.

Cellulose acetate electrophoresis showed derivatives A, B and C to be electrophoretically pure components which were mono-substituted by comparison with unsubstituted insulin and diacetoacetyl insulin prepared previously.

EXAMPLE 2

Reaction Of Insulin With Diketen

Zinc insulin (1.0 g.) as in Example 1, was dissolved to a final concentration of 0.167 mM in 0.1 M-HCl (45 ml.) and the pH adjusted with M-NaOH to 6.9 in the titration vessel of a Radiometer (type TTT1) pH-stat. Freshly distilled diketen was added in 5$\mu$ portions, the pH being maintained at 6.9 by the addition of alkali. When 1 equiv. of alkali was consumed, after approximately 5 minutes a sample was removed for ninhydrin analysis (Moore & Stein, 1954). Further portions of diketen were added until the ninhydrin colour yield had decreased by 30%. The amount of diketen added was 40$\mu$l (final concentration 0.49 mM).

The reaction mixture was made 0.2 M in $Na_2CO_3$—$NaHCO_3$ buffer, pH 9.5 and left overnight. After extensive dialysis against distilled water and freeze-drying, the yield of modified protein was 950 mg.

Chromatographic Separation of Acetoacetyl Insulins

The acetoacetyl insulins were separated on a column of DEAE-Sephadex A.25 (2.5 cm. × 40 cm.).

The column was equlibrated with buffer containing 0.01 M-tris and 0.05 M-NaCl in 7 M de-ionised urea adjusted to pH 7.20 with M-HCl. Acetoacetyl insulin (500 mg.) was dissolved in this buffer (50 mg./ml.) and the column was developed at a flow rate of 54.0 ml./hr., 12 ml. fractions being collected. After 120 ml. of eluant was collected a linear gradient, obtained by running 0.01 M-tris–0.15 M-NaCl in 7 M de-ionised urea at pH 7.20 into the stirred reservoir of the starting buffer was applied.

The mono-acetoacetylated insulins were re-chromatographed on a column of DEAE-Sephadex A-25 (2.5 cm. × 40 cm.) as described above with the exception that the starting buffer was adjusted to pH 7.30 with M-HCl. A linear gradient was applied by running 0.01 M-tris–0.10 M-NaCl in 7M de-ionised urea at pH 7.30 into the stirred reservoir of the starting buffer.

The protein concentration was determined from the extinction of the solution at 277 nm.

Figure 4:
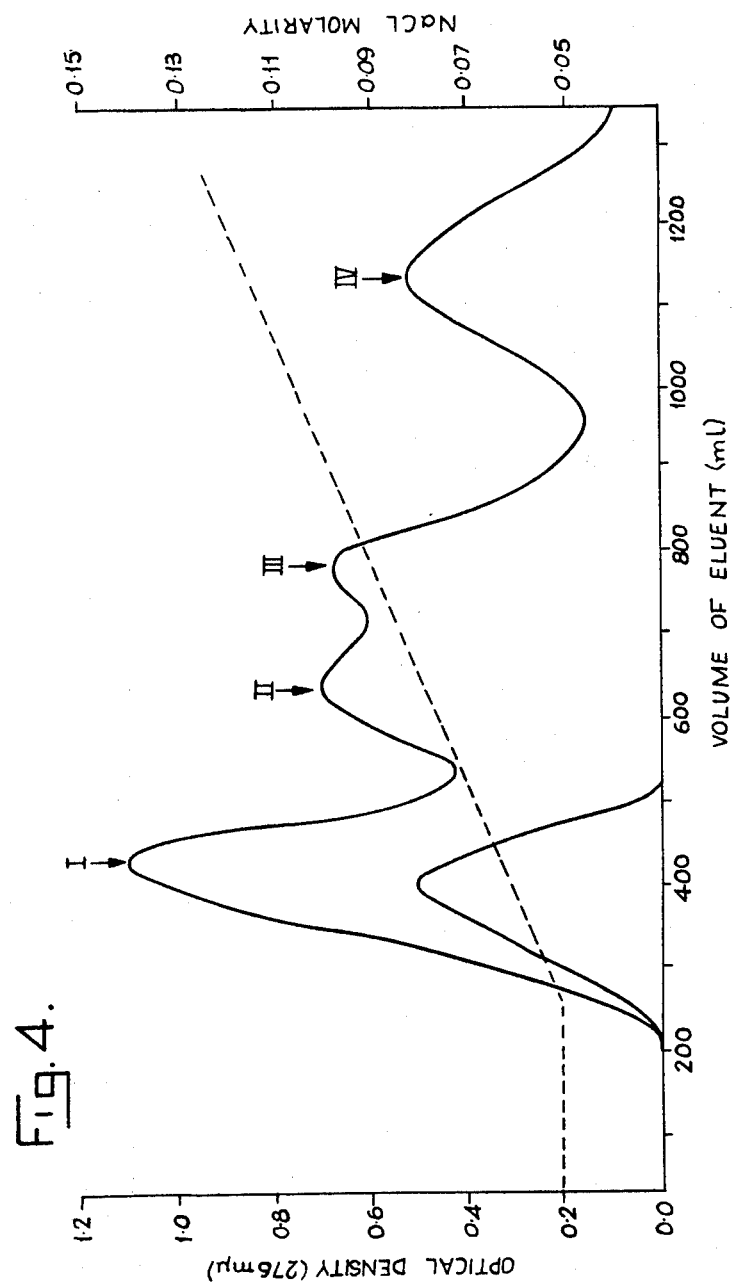

Chromatography results for insulin (500 mg.) treated with a threefold molar excess of diketen can be seen in FIG. 4. Four main peaks are discernible. The position of elution of unmodified insulin is shown on the Figure. Component I was mainly unmodified insulin; component IV (80 mg.) was chromatographically homogeneous, requiring a higher salt concentration for elution, and would be expected to be more highly substituted. No further protein was eluted.

EXAMPLE 3

N-Hydroxysuccinimide Acetate

Acetic acid (3.0 g. 0.05 mole) was dissolved in dichloromethane (30 ml.) and a solution of N-hydroxysuccinimide (5.76 g., 0.05 mole) in anhydrous dioxan (10 ml.) added. N,N'-dicyclohexylcarbodiimide (10.32 g., 0.05 mole) was added and the reaction mixture was stirred overnight at 4° and for a further 2 hours at room temperature. The dicyclohexylurea formed was filtered off and the solvent removed on a rotary evaporator under reduced pressure. Petroleum ether (60°–80°) was added to the supernatant until the solution went turbid. Filtration of the crystalline material and recrystallisation from ethyl acetate gave colourless needles of N-hydroxysuccinimide acetate (7.5 g., 95.5%) m.p. 131°–4°.

Reaction of Insulin With N-hyroxysuccinimide Acetate

Zinc insulin (200 mg., 0.038 mmol.) was dissolved in hydrochloric acid (40 ml., 0.1 M) and the pH adjusted with sodium hydroxide to 6.9 in the titration vessel of a Radiometer (Type TTT1) pH-stat. N-hydroxysuccinimide acetate (6 mg., 0.038 mmol.) was dissolved in dioxane (100μl) and added to the above solution in 10μl aliquots maintaining the pH at 6.9 by the addition of alkali every 30 minutes.

The reaction mixture was left overnight and was then dialysed against distilled water and lyophilised to yield 185 mg. of the modified protein.

In a second experiment, zinc insulin (500 mg. 0.085 mmol.) was treated with N-hydroxysuccinimide acetate (15.2 mg. 0.085 mmol.) at pH 8.5 exactly as described above, adding aliquots of the activated ester every 5 minutes.

In a further experiment, zinc insulin (500 mg., 0.085 mmol.) was treated with the activated ester (40 mg. 0.225 mmol.) at pH 8.5 as above.

Chromatographic Separation of the Acetyl Insulins

The acetyl insulins were separated on a column of DEAE-Sephadex A-25 (2.5 × 40 cm.) by a modification of the method described by Bromer & Chance (1967). This column was equilibrated with buffer containing 0.01M-tris and 0.05 M-NaCl in 7 M de-ionised urea adjusted to pH 7.30 with M-HCl. The acetyl insulins were dissolved in this buffer (50 mg./ml.) and the column was developed at a flow rate of 54.0 ml./hr., 9.7 ml. fractions being collected. 97 ml. of eluant was collected before a linear gradient was applied. For insulin treated with a molar equivalent of N-hydroxysuccinimide acetate, a linear gradient obtained by running 0.01 M-tris and 0.10 M-NaCl in 7 M de-ionised urea (1 l.) at pH 7.30 into the stirred reservoir of the starting buffer (1 l.) was applied.

For insulins treated with a threefold molar excess of N-hydroxysuccinimide acetate, the concentration of NaCl in the final buffer was increased to 0.15 M.

The protein concentration was determined from the extinction of the solution at 277 nm.

Tubes around the centre of each peak from the chromatography were pooled and separately rechromatographed under the same conditions. This process was repeated until each peak appeared homogeneous by iso-electric focussing. The material was lyophilised and the residue de-ionised on a column (1.5 × 60 cm.) of Sephadex G.10 equilibrated with 5% acetic acid. The fractions were pooled and the protein lyophilised.

Figure 5:
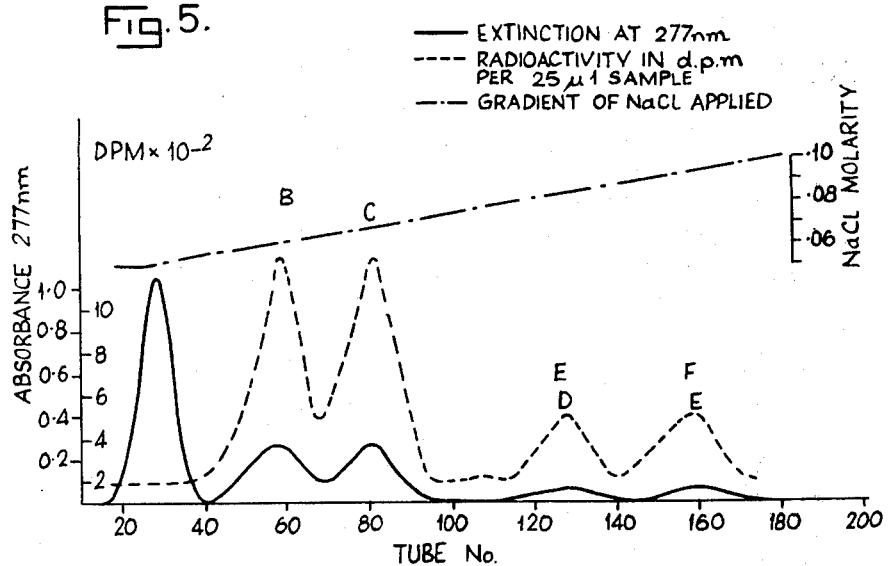
Figure 6:
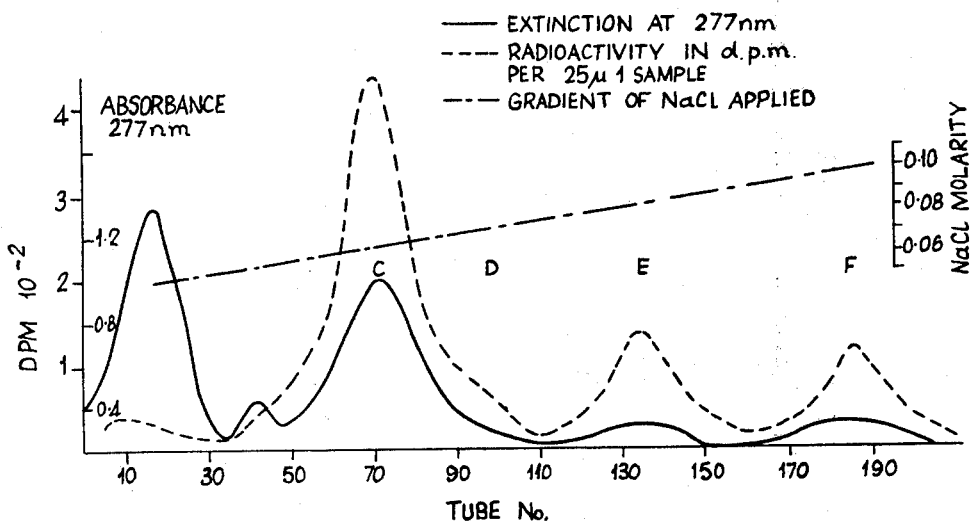

At low reagent concentrations and near neutral pH, the predominant products of the reaction are the two mono-substituted acetyl insulins in which the two terminal α-amino groups are modified (FIG. 5). However, if the pH is raised the amount of the $Phe^{B1}$ acetyl insulin isolated is reduced and $Lys^{B29}$ acetyl insulin is also produced (FIG. 6).

Figure 7:
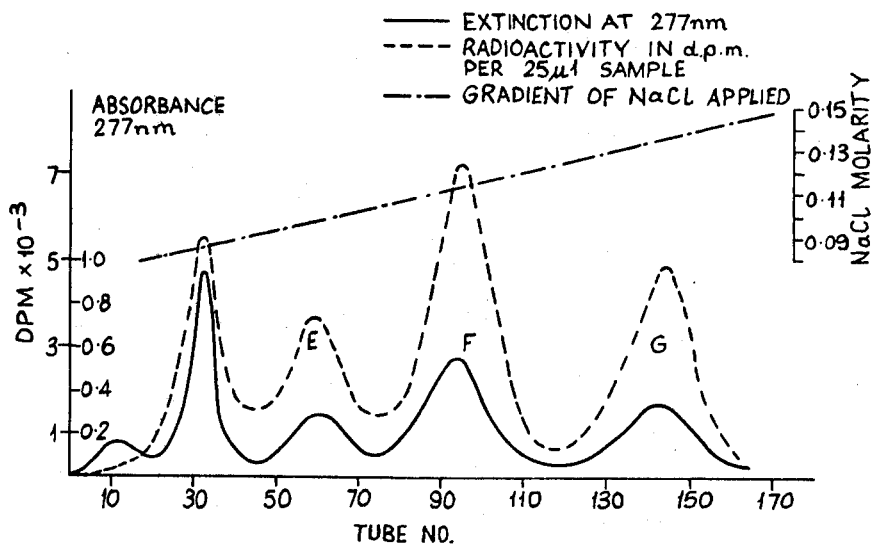

The chromatographic separation of the products of the reaction of insulin with a threefold excess of the activated ester at pH 8.5 can be seen in FIG. 7. Characterisation of the two di-substituted acetyl insulins formed shows that they are $Phe^{B1}$ $Gly^{A1}$-diacetyl insulin and $Gly^{A1}$ $Lys^{B29}$-diacetyl insulin respectively.

Biological Assay

The insulin derivatives were separated from trace amounts of urea and salt by elution from a Sephadex G.10 column (2.5 × 60 cm.) equilibrated with 5% aqueous acid and the protein, after lyophilisation, was dried over phosphorous pentoxide at room temperature for 2 days. The derivatives were assayed against a neutral insulin solution (Nuso insulin batch A 354) as standard by the Mouse Convulsion method (British Pharmacopoeia, 1968). All injections were of solutions in acetate buffer, pH 8.0.

EXAMPLE 4

The procedures described in Examples 1, 2 and 3 were repeated using bovine insulin in place of porcine insulin. Virtually identical results were obtained in all cases.

EXAMPLE 5

Following the procedures described in Examples 1(b) and 1(c), the mono-carbamyl, mono-methylcarbamyl and monomethylthiocarbamyl derivatives of bovine insulin were prepared by reacting zinc insulin (600 mg., 100μ mole) in 100 mM phosphate buffer pH 7.5 (40 ml.) at 37°C. overnight with potassium cyanate and methyl isocyanate and methyl isothiocyanate (150μ moles) respectively and subsequently extensively dialysed and then separated by chromatography as described above. The desired substituted derivatives of the $B_1$ amino acid and other residues were isolated and dialysed to remove excess salts and freeze dried.

EXAMPLE 6

Following the procedure of Examples 1(b) and 1(c), insulin was reacted with methyl acetimidate hydrochloride and the resulting products were worked up as described previously.

EXAMPLE 7

Preparation of $A_1$, $B_1$, $B_{29}$-triacetyl-insulin

Insulin (100 mg., 16.7μ mole) is dissolved in anhydrous dimethylformamide (100 ml.) and redistilled triethylamine (0.5 ml.) added. N-hydroxysuccinimide acetate (130 mg., 0.84 mmole) is dissolved in dimethylformamide (1.2 ml.) and is added to the stirred insulin solution in 0.1 ml. aliquots, over a period of 60 minutes. The solution is stirred overnight and then dialysed extensively against distilled water and the dialysed solution lyophilised Yield of $A_1$, $B_1$, $B_{29}$ triacetyl-insulin (90 mg.)

EXAMPLE 8

(Carbamyl-Phe)B₁-insulin 600 mg. of amorphous Zn-free insulin is dissolved in 60 ml. of 0.1 molar phosphate buffer (pH 7.5); 0.3 ml. of 0.6N potassium cyanate is added thereto and the mixture maintained at 30°C. for 18 hours. The reaction solution is then dialysed against water until free of excess cyanate as well as buffer salts and thereafter freeze-dried. Yield: 500 mg. In order to separate the (carbamyl-Phe)B₁-insulin, the usual methods of peptide purification can be employed, such as ion exchange chromatography, for example with the use of DEAE-Sephadex in 4–7 molar urea buffer, or countercurrent distribution, e.g. in the system n-butanol (20), methanol (5), water (20), glacial acetic acid (1). The yield in pure (carbamyl-Phe)B₁-insulin is 200 mg.

Paper electrophoresis:

Conditions: 24 molar aqueous formic acid/4 molar aqueous urea, pH 2, dyeing with Pauly reactant. 300μg was applied.

The substance migrates as a uniform band; the Rf value of 0.91 (insulin: 1.00) for this compound corresponds to a monosubstituted insulin.

EXAMPLE 9

(Carbamyl-Gly)A₁-(Carbamyl-Phe)B₁-insulin 6 g of amorphous, Zn-free insulin from cattle is dissolved in 600 ml. of demineralised water; the solution is adjusted to pH 7.2 with 1N NaOH and heated to 30°C. At this temperature, over a period of about 7 hours, 300 ml. of 0.6N potassium cyanate is added dropwise to the stirred reaction mixture. During the same interval, the pH is gradually brought from 7.2 to 5.5 by the addition of 1N acetic acid using an automatic titrating device. After termination of the reaction, excess cyanate is destroyed by acidification to a Ph of 2.2–2.5. The acidic solution is dialysed against distilled water until free of excess acid and salts and subsequently freeze-dried. The yield is 5.3–5.5 g of (carbamyl-Gly)A₁-(carbamyl-Phe)B₁-insulin. Minor amounts of mono- and tricarbamyl insulin can be removed by the usual methods of peptide purification, such as ion exchange chromatography, countercurrent distribution, carrier-free electropboresis, or advantageously by isoelectric precipitation by dissolving the product in water at pH 7 and precipitating it by acidification to pH 4; the mono- and tricarbamyl insulin impurities remain in solution and can be decanted off.

Paper electrophoresis:

The substance migrates as a uniform band. The Rf value is 0.76 (insulin: 1.00) using the conditions of Example 1.

EXAMPLE 10

(Carbamyl-Gly)A₁-(Carbamyl-Phe)B₁-(Carbamyl-Lys)B₂₉-insulin 6 g of amorphous, Zn-free insulin is dissolved in 600 ml. of a pH 8.5 buffer (e.g. tris buffer or phosphate buffer), and 300 ml. of 0.6N potassium cyanate is gradually added dropwise thereto with stirring. After the addition is terminated, excess cyanate is destroyed by acidification to pH 2.5. The acidic solution is dialysed against distilled water until free of excess acid and thereafter freeze-dried. Yield: 5.5 g. Purification is generally unnecessary, but can readily be effected according to the usual methods.

Paper electrophoresis:

Using the condition of Example 1, the substance migrates as a uniform band. The Rf value thereof is 0.56 (insulin: 1.00) and corresponds to a tri-substituted insulin.

We claim:

1. A pharmaceutical composition useful for treating diabetes in humans which comprises a hypoglycemically effective amount of a mono-, di- or tri-substituted insulin in which the terminal amino group of the B chain (B₁ phenylalanine) is protected by an acyl or other blocking substituent containing up to 7 carbon atoms selected from the group consisting of formyl, acetyl, trifluoroacetyl, cyclopropane-carbonyl, acetoacetyl, benzoyl, 2,2-dimethyl-3-formyl-L-thiazolidine-4-carbonyl, carbamyl, methylcarbamyl, thiocarbamyl, methylthiocarbamyl,

HOCH₂CH₂CO—, HOOCCH₂CO— and H₂NOCCH₂CO—, the terminal amino group of the A chain (A₁ glycine) is either free or protected by an acyl or other blocking substituent containing no more than 4 carbon atoms and no free primary amino group selected from the group consisting of formyl, acetyl, trifluoroacetyl, cyclopropane-carbonyl, acetoacetyl, carbamyl, methylcarbamyl, thiocarbamyl, methylthiocarbamyl,

HOCH₂CH₂CO—, HOOCCH₂CO— and H₂NOC—CH₂CO— and the amino group of the B₂₉ amino acid (lysine) is either free or protected by an acyl or other blocking substituent containing no more than 4 carbon atoms and no free primary amino group selected from the group consisting of formyl, acetyl, trifluoroacetyl, cyclopropanecarbonyl, acetoacetyl, carbamyl, methylcarbamyl, thiocarbamyl, methylthiocarbamyl,

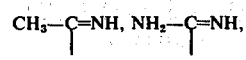

HOCH₂CH₂CO—, HOOC—CH₂—CO— and H₂NO-C—CH₂CO— in combination with a pharmaceutically acceptable diluent.

2. A composition according to claim 1 in which the terminal amino group of the A chain (A₁ glycine) is either free or protected by an acyl or other blocking substituent containing no more than three atoms other than hydrogen selected from the group consisting of formyl, acetyl, carbamyl, thiocarbamyl,

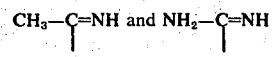

and the amino group of the B₂₉ amino acid (lysine) is either free or protected by an acyl or other blocking substituent containing no more than three atoms other than hydrogen selected from the group consisting of formyl, acetyl, carbamyl, thiocarbamyl,

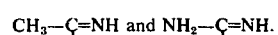

3. A composition according to claim 1 in which the $B_1$ amino acid is protected by acetyl or acetoacetyl.

4. A composition according to claim 1 in which the $B_1$ amino acid is protected by 2,2-dimethyl-3-formyl-L-thiazolidine-4-carbonyl.

5. A composition according to claim 1 in which at least one of the substituents is a carbamyl group.

6. A composition according to claim 1 wherein the insulin is mono-substituted.

7. A composition according to claim 1 wherein the insulin is di-substituted.

8. A composition according to claim 1 wherein the insulin is tri-substituted.

9. A composition according to claim 1 wherein the $A_1$ and $B_1$ protective substituents are the same.

10. A composition according to claim 1 wherein the insulin is $B_1$(phenylalanine)-N-monocarbamyl insulin.

11. A composition according to claim 1 wherein the insulin is $A_1$(glycine) $B_1$(phenylalanine)-N,N'-dicarbamyl insulin.

12. A composition according to claim 1 wherein the insulin is $A_1$(glycine)$B_1$(phenylalanine)$B_{29}$(lysine)-N,N',N''-tricarbamyl insulin.

13. A pharmaceutical composition according to claim 1 in injectable form.

14. A composition according to claim 8 wherein the substituents are the same.

15. A pharmaceutical composition useful for treating diabetes in humans which comprises a hypoglycemically effective amount of a mixture of $A_1$(glycine), $B_1$(phenylalanine), $B_{29}$(lysine)-N,N',N''-tricarbamyl insulin and $A_1$(glycine), $B_1$(phenylalanine)-N,N'-dicarbamyl insulin in combination with a pharmaceutically acceptable diluent.

16. A method of treating diabetes in humans which comprises parenterally administering to such human a hypoglycemically effective amount of a mono-, di- or tri-substituted insulin in which the terminal amino group of the B chain ($B_1$ phenylalanine) is protected by an acyl or other blocking substituent containing up to 7 carbon atoms selected from the group consisting of formyl, acetyl, trifluoroacetyl, cyclopropane-carbonyl, aceto-acetyl, benzoyl, 2,2-dimethyl-3-formyl-L-thiazolidine-4-carbonyl, carbamyl, methylcarbamyl, thiocarbamyl, methylthiocarbamyl,

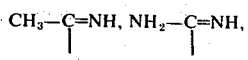

$HOCH_2CH_2CO—$, $HOOCCH_2CO—$ and $H_2NOCCH_2CO—$, the terminal amino group of the A chain ($A_1$ glycine) is either free or protected by an acyl or other blocking substituent containing no more than 4 carbon atoms and no free primary amino group selected from the group consisting of formyl, acetyl, trifluoroacetyl, cyclopropane-carbonyl, acetoacetyl, carbamyl, methylcarbamyl, thiocarbamyl, methylthiocarbamyl,

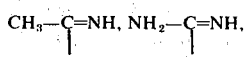

$HOCH_2CH_2CO—$, $HOOCCH_2CO—$ and $H_2NOC—CH_2CO—$ and the amino group of the $B_{29}$ amino acid (lysine) is either free or protected by an acyl or other blocking substituent containing no more than 4 carbon atoms and no free primary amino group selected from the group consisting of formyl, acetyl, trifluoroacetyl, cyclopropanecarbonyl, acetoacetyl, carbamyl, methylcarbamyl, thiocarbamyl, methylthiocarbamyl,

$HOCH_2CH_2CO—$, $HOOC—CH_2—CO—$ and $H_2NO-C—CH_2CO—$.

17. A method according to claim 16 in which the terminal amino group of the A chain ($A_1$ glycine) is either free or protected by an acyl or other blocking substituent containing no more than three atoms other than hydrogen selected from the group consisting of formyl, acetyl, carbamyl, thiocarbamyl,

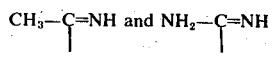

and the amino group of the $B_{29}$ amino acid (lysine) is either free or protected by an acyl or other blocking substituent containing no more than three atoms other than hydrogen selected from the group consisting of formyl, acetyl, carbamyl, thiocarbamyl,

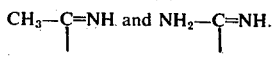

18. A method according to claim 16 in which the $B_1$ amino acid is protected by acetyl or acetoacetyl.

19. A method according to claim 16 in which the $B_1$ amino acid is protected by 2,2-dimethyl-3-formyl-L-thiazolidine- 4-carbonyl.

20. A method according to claim 16 in which at least one of the substituents is a carbamyl group.

21. A method according to claim 16 wherein the insulin is mono-substituted.

22. A method according to claim 16 wherein the insulin is di-substituted.

23. A method according to claim 16 wherein the insulin is tri-substituted.

24. A method according to claim 17 wherein the $A_1$ and $B_1$ protective substituents are the same.

25. A method according to claim 16 wherein the insulin is $B_1$(phenylalanine-N-monocarbamyl insulin.

26. A method according to claim 16 wherein the insulin is $A_1$(glycine)$B_1$(phenylalanine)-N,N'-dicarbamyl insulin.

27. A method according to claim 16 wherein the insulin is $A_1$(glycine)$B_1$(phenylalanine)$B_{29}$(lysine)-N,N',N''-tricarbamyl insulin.

28. A method according to claim 13 wherein the substituents are the same.

29. A method of treating diabetes in humans which comprises parenterally administering to such human a hypoglycemically effective amount of a mixture of $A_1$(glycine), $B_1$(phenylalanine), $B_{29}$(lysine)-N,N'N''-tricarbamyl insulin and $A_1$(glycine), $B_1$(phenylalanine)-N,N'-dicarbamyl insulin.

* * * * *